US006436680B1

(12) United States Patent
Guezennec et al.

(10) Patent No.: US 6,436,680 B1
(45) Date of Patent: Aug. 20, 2002

(54) MARINE BACTERIAL STRAIN OF THE GENUS VIBRIO, WATER-SOLUBLE POLYSACCHARIDES PRODUCED BY SAID STRAIN AND THEIR USES

(75) Inventors: Jean Guezennec, Plouzane; Patricia Pignet, Brest; Gérard Raguenes, Brest; Hélène Rougeaux, Brest, all of (FR)

(73) Assignee: Instit Francais de Recherche pour l'Exploitation de la Mer, Issy Les Moulineaux (FR)

( * ) Notice: Subject to any disclaimer, the term of this patent is extended or adjusted under 35 U.S.C. 154(b) by 0 days.

(21) Appl. No.: 09/380,079

(22) PCT Filed: Feb. 25, 1998

(86) PCT No.: PCT/FR98/00368
§ 371 (c)(1),
(2), (4) Date: Nov. 19, 1999

(87) PCT Pub. No.: WO98/38327
PCT Pub. Date: Sep. 3, 1998

(30) Foreign Application Priority Data

Feb. 25, 1997 (FR) .............................. 97 02199

(51) Int. Cl.$^7$ .............................. C12P 19/04; C12P 1/00; C12P 19/00; C12N 1/12; C12N 1/00
(52) U.S. Cl. ....................... 435/101; 435/41; 435/72; 435/822; 435/909; 435/252.1
(58) Field of Search ................. 435/252.1, 41, 435/72, 822, 101, 909

(56) References Cited

U.S. PATENT DOCUMENTS 5,393,777 A 2/1995 Crosa

FOREIGN PATENT DOCUMENTS

WO WO94 18340 8/1994

OTHER PUBLICATIONS

Database WPI, Derwent Publications Ltd., XP002048325, Week 7750, Publication No. JP 50 132 189 to Mitsubishi Kasei Corp.
Database WPI, Derwent Publications Ltd., XP002048326, Week 8504, Publication No. JP 59 220 197 to Snow Brand Milk Pro Co Ltd.
G. Raguenes et al., "Vibrio Diabolicus Sp. Nov., A New Polysaccharide–Secreting Organism Isolated Form a Deep–Sea Hydrothermal Vent Polychaete Annelid, Alvinella Pompejana", *International Journal of Systematic Bacteriology*, Oct. 1, 1997, pp. 989–995, vol. 47, No. 4, Washington, DC.
Singleton and Sainsbury, Dictionary of Microbiology and Molecular Biology, p. 565, col. 2, Line 30, 1991.*

* cited by examiner

Primary Examiner—Francisco Prats
Assistant Examiner—Kailash C. Srivastava
(74) Attorney, Agent, or Firm—Alston & Bird LLP

(57) ABSTRACT

The invention concerns a hydrothermal bacterial strain of marine origin, belonging to the genus Vibrio, and an exopolysaccharide produced by said strain. Said exopolysaccharide is useful in particular for preparing medicines.

7 Claims, 4 Drawing Sheets

MARINE BACTERIAL STRAIN OF THE GENUS VIBRIO, WATER-SOLUBLE POLYSACCHARIDES PRODUCED BY SAID STRAIN AND THEIR USES

The present invention relates to a new bacterial strain of the genus Vibrio, to the exopolysaccharides produced by the said strain and to their uses.

Some microorganisms obtained from the deep submarine hydrothermal medium produce biomolecules whose particular structure and composition confer on them properties of great potential industrial interest; among these biomolecules are a wide variety of polysaccharides some of which have already been the subject of studies intended to determine their structures and their properties.

The studies mentioned below have related more specifically to the exopolysaccharides (EPS) excreted by bacteria of the genus Alteromonas which are cultured under laboratory conditions, and in particular on glucose-enriched medium.

VINCENT et al. [Appl. Environ. Microbiol., 60, 4134–4141 (1994)] have thus described an exopolysaccharide, called EPS-1545, excreted by a strain, designated by the reference HYD-1545, of a bacteria of the genus Alteromonas. The EPS obtained by ethanol precipitation comprises between 49 and 55% of neutral monosaccharides, and between 32.5 and 39% of uronic acids.

GUEZENNEC et al., [Carbohydrate Polymers, 24, 287–294 (1994)] have classified the EPSs produced by various bacteria of the genus Alteromonas into 5 different groups on the basis of their composition: group 1 consists of EPS comprising between about 50 and 60% of neutral monosaccharides, about 10% of uronic acids, between 0.5 and 3.7% of osamines, and between 11.5 and 21.5% of sulphates; group 2 consists of EPS comprising about 50% of neutral monosaccharides, possessing a low content of uronic acids (8%), comprising between 1 and 3.2% of osamines, and whose content of sulphates is between less than 10% and 13%; the group 3 EPSs comprise between 40 and 50% of neutral monosaccharides, have a very low content of uronic acids (between S and 7%), comprise between 1.2 and 1.7% of osamines, and have a content of sulphates varying between 8.9 and 17.2; group 4 consists of EPS comprising 46 to 49% of neutral monosaccharides, possessing a high content of uronic acids (between 34 and 40%), comprising between 0.2 and 1.6% of osamines, and having a content of sulphates of between 9.7 and 13%; group 5 consists of EPS having a relatively low content of neutral monosaccharides (38 to 47%), a high content of uronic acids (26 to 32%), comprising between 1 and 1.6% of osamines, and between 5.2 and 10.1% of sulphates; one of the EPSs of this group comprises, in addition, one hexuronic acid carrying a lactate substituent.

A number of the strains and polymers described in the publications by VINCENT et al. and GUEZENNEC et al. cited above are the subject of application PCT FR 94/00169 published under WO 94/18340.

Recently, RAGUENES et al. [Appl. Environ. Microbiol, 62, 67–73 (1996)] have described an EPS, different from the preceding ones, which is obtained from a bacterium of the genus Alteromonas (*Alteromonas macleodii* subsp. fijiensis). This EPS comprises about 38% of neutral monosaccharides, 38% of uronic acids, 2.3% of osamines and about 5% of sulphates.

The inventors, continuing their research studies on bacteria obtained from the deep submarine hydrothermal medium have now isolated from Pompei worm (*Alvinella pompejana*) a new strain, called HE800, belonging to the genus Vibrio. This strain, which was deposited on Oct. 17, 1995 at the CNCM (Collection Nationale de Cultures de Microorganismes, 28, rue du Docteur Roux, 75724 PARIS, FRANCE) under number I-1629, represents a new species of Vibrio, for which the name *Vibrio diabolicus* is proposed.

*Vibrio diabolicus* is a Gram-negative bacillus, about 0.8 $\mu$wide and 2.2 $\mu$m long; it is mobile with the aid of a polar flagellum in liquid medium and of peritrichous flagella in solid medium; it is a non-encapsulated, non-pigmented and non-luminescent bacterium.

It is a catalase+, cytochrome oxidase+, chitinase+, facultative anaerobic bacterium. It reduces nitrates to nitrites. It is sensitive to the vibriostatic agent 0/129 (2, 4-diamino-6, 7-diisopropylpteridine).

It uses a wide variety of carbon substrates; it can use in particular, as sole carbon source, any one of the following substrates: glycerol, ribose, galactose, glucose, fructose, mannose, mannitol, N-acetylglucosamine, maltose, sucrose, trehalose, starch, glycogen, gluconate, caprate, citrate and malate.

Its growth is optimum at a temperature of between 30 and 45° C., a pH of between 7 and 8, and a salinity of between 20 and 50 g/l of NaCl; its generation time under these conditions is between 18 and 28 minutes.

The G+C content of its DNA is 49.6%. The phylogenic analysis of the 16S rRNA gene (according to the protocol established by RUIMY et al. [Int. J. Syst. Bacteriol 44, 416–426 (1994)] have made it possible to establish that it belongs to a well-defined taxon which also includes *Vibrio mytili*, *Vibrio nereis* and *Vibrio tubiashii*. The results of this analysis are illustrated by FIG. 1. The percentage homology of the DNA of the HE800 strain with that of the 3 most closely related Vibrio mentioned above is 27%, 15% and 5%, respectively.

Table I below illustrates the metabolic properties of the HE800 strain (only the positive responses are included in this table)

TABLE I

| | |
|---|---|
| Assimilation of glycerol | + |
| Assimilation of ribose | + |
| Assimilation of galactose | + |
| Assimilation of glucose | + |
| Assimilation of fructose | + |
| Assimilation of mannose | + |
| Assimilation of mannitol | + |
| Assimilation of N-acetylglucosamine | + |
| Assimilation of maltose | + |
| Assimilation of sucrose | + |
| Assimilation of trehalose | + |
| Assimilation of starch | + |
| Assimilation of glycogen | + |
| Assimilation of gluconate | + |
| Assimilation of caprate | + |
| Assimilation of citrate | + |
| Assimilation of malate | + |
| Reduction of nitrates to nitrites | + |
| Production of indole | + |
| Acidification of glucose | + |
| Hydrolysis of esculin (β-glucosidase) | + |
| Hydrolysis of gelatin (protease) | + |
| b-galactosidase (PNPG) | + |
| Lysine decarboxylase | + |
| Ornithine decarboxylase | + |
| Tryptophan deaminase | + |
| Alkaline phosphatase | ++ |
| Esterase (C4) | + |
| Esterase lipase (C8) | +++ |
| Leucine arylamidase | +++ |

TABLE I-continued

| | |
|---|---|
| Trypsin | + |
| Chymotrypsin | + |
| Acid phosphatase | +++ |

The above morphological, biochemical and phylogenetic characteristics make it possible to include the HE800 strain in the genus Vibrio [BAUMANN et al.: Genus Vibrio, Bergey's Manual of Systematic Bacteriology, Vol. 1, 342–352. (1984) KRIEG, and HOIT (ed.); The Williams and Wilkins Co., Baltimore].

Because the DNA/DNA percentage homology with the three subspecies of the abovementioned genus Vibrio is less than 30%, the HE800 strain may be considered as representing a new species of Vibrio [WAYNE et al., Report of the Ad Hoc Committee on reconciliation of approaches to bacterial systematics, Int. J. Syst. Bacteriol. 463–464, (1987)], for which the name: *Vibrio diabolicus* is proposed.

The subject of the present invention is strains of bacteria possessing the above-defined characteristics of the species *Vibrio diabolicus*, and in particular the HE800 strain; this includes in particular bacteria whose DNA has a percentage homology greater than 28%, preferably greater than 30%, and advantageously greater than 50%, with the DNA of the HE800 strain. This subject also includes the bacteria obtained from bacteria of the species *Vibrio diabolicus*, and in particular of the strain HE800, by mutation, or by genetic recombination, such as for example bacteria of the species *Vibrio diabolicus* harbouring a plasmid carrying a heterologous gene.

The present invention also includes the various products which may be obtained from the said bacteria, which comprises in particular their cellular fractions, the enzymes as well as the nucleic acid preparations which may be extracted therefrom, as well as the products excreted or secreted by these bacteria.

This comprises polysaccharides capable of being obtained from Vibrio diabolicus culture supernatants, and in particular an exopolysaccharide capable of being obtained by ethanol precipitation, from culture supernatants of the HE800 strain.

The analysis carried out by the inventors of an exopolysaccharide in accordance with the present invention, produced by the HE800 strain, reveals the following characteristics, determined from a preparation of the said polysaccharide comprising about 1% by weight of proteins:
- it does not comprise neutral monosaccharides;
- its content of osamines is about 30±5% by weight;
- its content of uronic acids is about 32±5% by weight;
- its monosaccharide composition, determined after acid methanolysis, is the following: about 11.2% by weight of glucuronic acid, about 18% by weight of N-acetylglucosamine, about 7.9% by weight of N-acetylgalactosamine, that is to say 1.4 mol of N-acetylglucosamine and 0.6 mol of N-acetylgalactosamine per 1 mol of glucuronic acid;
- it does not comprise sulphated saccharide units;
- its intrinsic viscosity is of the order of 570 ml/g;
- its mean molecular weight is of the order of 800,000 Da.

This polysaccharide possesses a composition similar to that of heparin, which is commonly used in the pharmaceutical industry, in particular for its anticoagulant and antithrombotic properties. It however differs therefrom in particular by the presence of N-acetylgalactosamine and by the absence of sulphate groups.

The subject of the present invention is also fractions of the polysaccharide defined above, and in particular low-molecular weight, and highly sulphated, fractions.

Because of its structure, this polysaccharide can be used in particular in the context of the pharmaceutical industry, for example as raw material in the context of the production of medicaments. For this purpose, it may for example be modified, in particular by the chemical or enzymatic route in order to obtain fractions which are sulphated, and:or of low molecular weight, which can be used for example as antiviral, antitumour or antithrombotic agents.

The present invention will be understood more clearly with the aid of the additional description which follows, which refers to examples describing the preparation and the characterization of polysaccharides in accordance with the invention.

It goes without saying, however, that these examples are given solely by way of illustration of the subject of the invention and do not in any manner constitute a limitation thereto.

EXAMPLE 1

Figure 1:
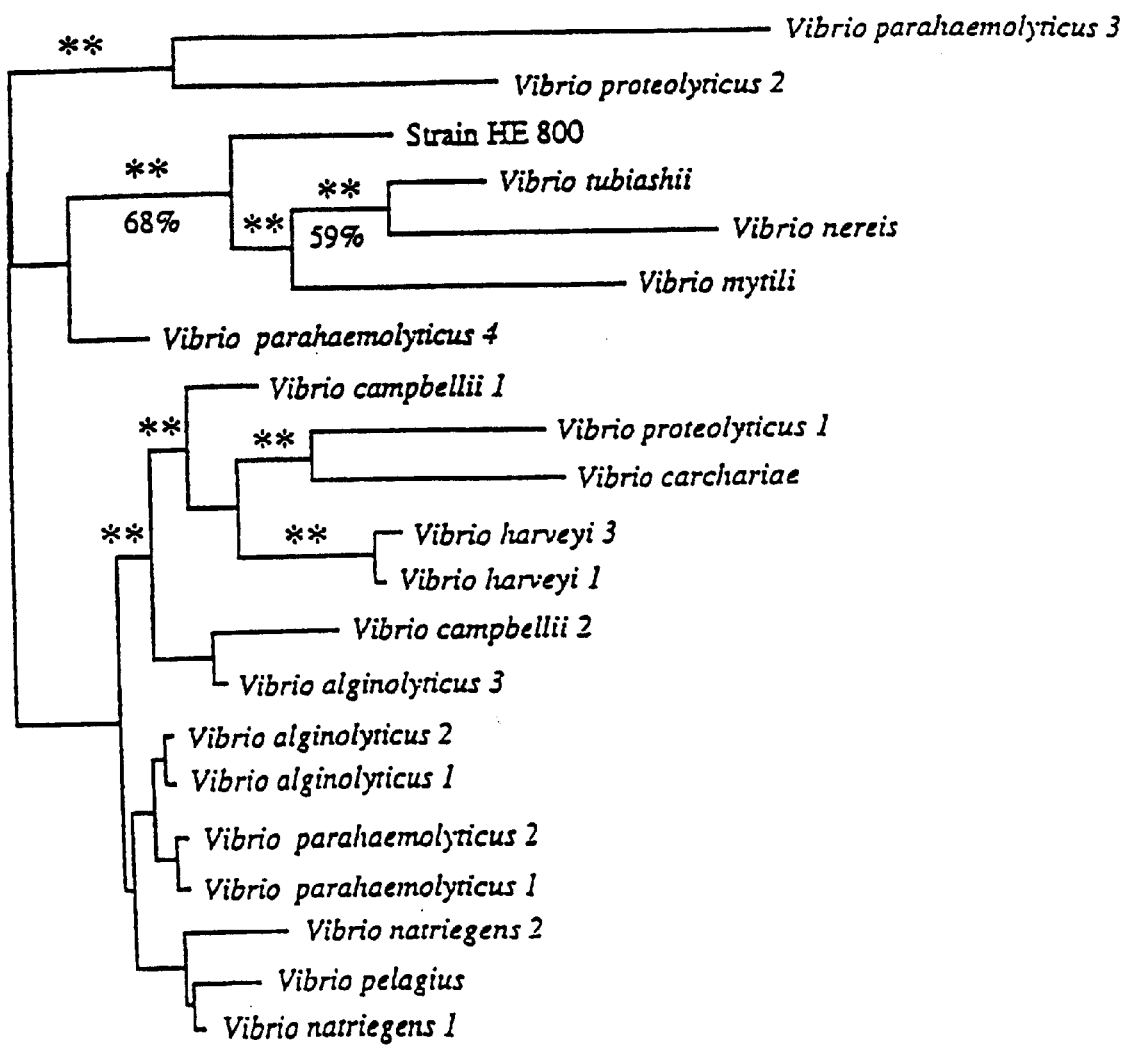
FIG. 1 depicts the Phylogenic Analysis of the 16S rRNA gene.

Preparation of Exopolysaccharides from Vibrio Diabolicus Cultures a) Cultures of Vibrio diabolicus The HE800 strain is cultured on a 2216E medium [OPPENHEIMER, J. Mar. Res. 11, 10–18 (1952)] enriched with glucose (30 g/l). The production is carried out at 30° C. and at pH 7.4 in a 2-litre fermenter containing 1 litre of glucose-containing 2216E medium. After 48 hours of culture, the broth has a low viscosity (of the order of 40 centipoises at 60 rpm).

b) Purification of the exopolysaccharide

The bacteria are separated from the broth by centrifugation at 20,000 g for 2 hours, and then the polysaccharide is precipitated from the supernatant with the aid of pure ethanol, and then several ethanol/water washes are carried out with increasing proportions of ethanol, according to the method described by TALMONT et al. [Food Hydrocolloids 5, 171–172 (1991)] or VINCENT et al. [Appl. Environ. Microbiol., 60, 4134–4141 (1994)]. The polymer obtained is dried at 30° C. and stored at room temperature. 2.5 g of purified polysaccharide per litre of culture were thus obtained.

EXAMPLE 2

Physicochemical Characterization of the Exopolysaccharide Produced by the Bacterium Vibrio Diabolicus a) Chemical analysis:

The contents of neutral monosaccharides, acidic monosaccharides, amine monosaccharides and proteins of the polysaccharide obtained as described in Example 1 above are determined according to the following calorimetric methods:

Assay of the Neutral Monosaccharides

Method of TILLMANS and PHILLIPPI [Biochem. J., 215, 36–60, (1929)] modified by REMINGTON [Biochem. J., 25, 1062–1071, (1931)].

Modification made: to remove the interference due to uronic acids, these are assayed by the method of DISCHE [J. Biol Chem. 167, 189–198, (1947); MONTREUIL J. and SPIK G., Méthodes colorimétriques de dosage des glucides totaux—Microdosage des glucides [Colorimetric methods of assaying total carbohydrates—microassay of carbohydrates], part 1. (1963)].

Reagent: sulphuric orcinol

Reference: 1 mannose/1 galactose

Assay of the Acidic Monosaccharides

Two methods were used
1) DISCHE method (1947; reference cited above).

Modification made: in order to remove the interference due to the hexoses, these are assayed, as mentioned above, by the method of TILLMANS and PHILLIPPI (1929) modified by REMINGTON (1931).

Reagent: carbazole

Reference: glucuronic acid

2) Method of BLUMENKRANTZ and ASBOE-HANSEN [Anal. Biochem. 54, 484–489, (1973)].

Reagents: 0.0125 M sodium meta-hydroxydiphenyl-tetraborate in concentrated sulphuric acid Reference: glucuronic acid.

Assay of the osamines

Method of ELSON and MORGAN [Biochem. J. 27, 1824–1828 (1933)] modified by BELCHER et al. (Modification of the composition of the EHRLICH reagent).

Modification made: conversion of the EHRLICH reagent according to the method of BLIX (MONTREUIL and SPIK, Microassay of the carbohydrates, part 1, 1963).

Reagents: alkaline solution of acetylacetone Ehrlich reagent

Reference: glucosamine.

Assay of the proteins

Method of LOWRY [LOWRY et al. [J. Biol. Chem. 193, 265–275, (1953)].

Reagents: Reagent A Reagent B

FOLIN-CIOCALTEU reagent: 1N

Reference: bovine albumin.

The polysaccharide is subjected to acid methanolysis so as to put them in the form of N-acetylated or O-trimethylsilylated methylglycosides according to the method of KAMERLING et al., [Biochem. J., 151, 491–495, (1975)], modified by MONTREUIL [MONTREUIL et al., Glycoproteins, in Carbohydrate Analysis: A practical approach: Eds CHAPLIN and KENNEDY, IRL Press, Oxford, Washington DC, p. 143–204, (1986)].

The various sugars obtained are then analysed by gas chromatography, where appropriate, by gas chromatography/mass spectrometry coupling. These analyses show the presence of glucuronic acid, N-acetylglucosamine and N-acetylgalactosamine in proportions by weight of 11.2%, 18% and 7.9% respectively. Galacturonic acid is also detected in a low quantity (0.5% by weight). The neutral monosaccharides (glucose and mannose) are only detected in trace quantities, probably reflecting a contamination.

b) Spectroscopic analysis: NMR and infrared spectroscopy.

The presence of acetate and carboxyl groups was investigated by Nuclear Magnetic Resonance (NMR) and Fourier Transformed Infrared Spectroscopy. The latter method makes it possible, in addition, to quantify the potential content of sulphates (LIJOUR et al., 1994, Anal. Biochem., 220, 244–248).

Figure 2:
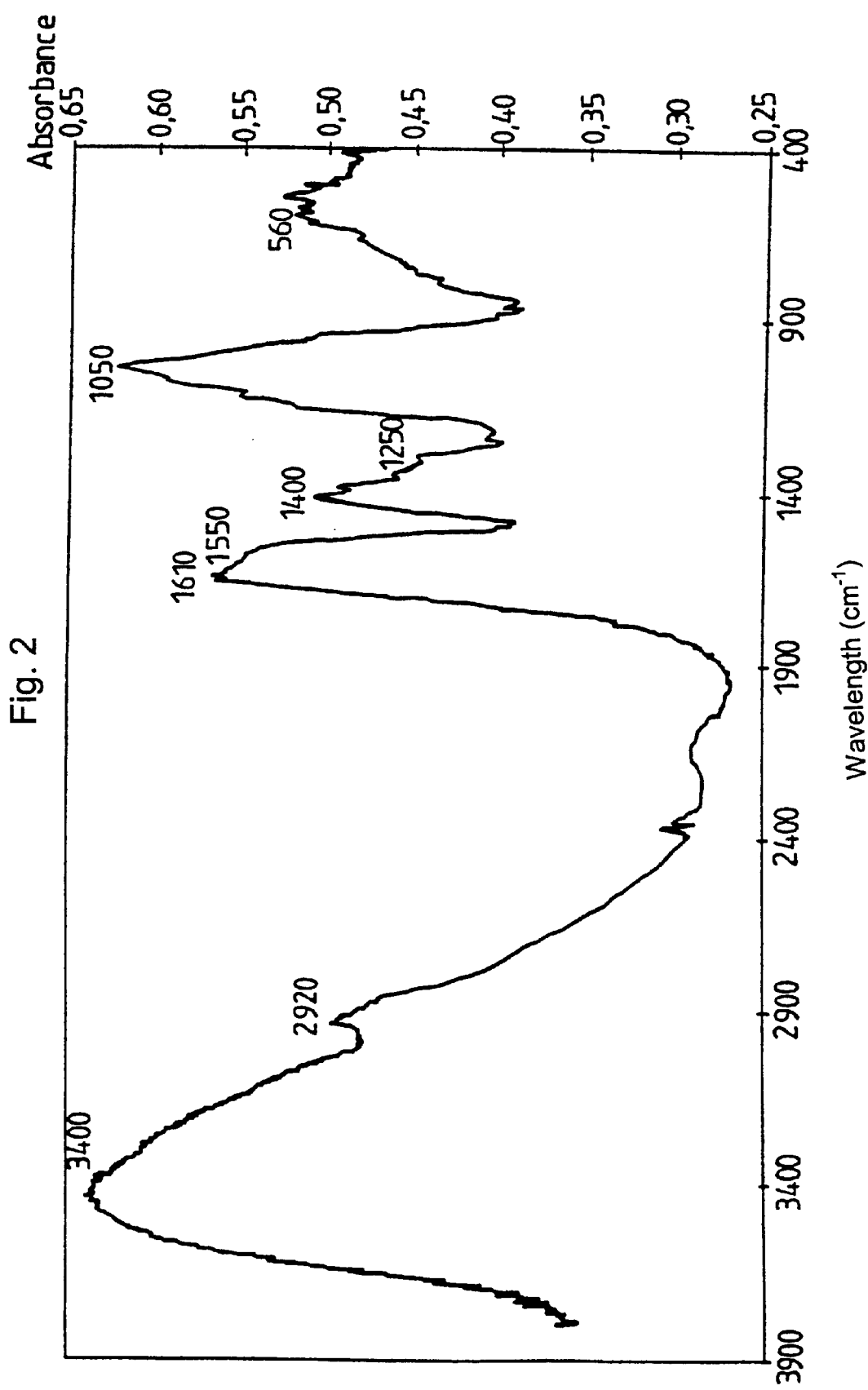
FIG. 2 depicts the Infrared Spectrum of the Exopolysaccharide of *Vibrio diabolicus*.

The infrared spectrum is represented in FIG. 2.

This spectrum makes it possible to identify carboxylated and N-acetylated groups, which confirm the presence of uronic acids. The absence of sulphate groups is in addition observed.

The NMR analyses ($^{13}$C and $^1$H) also confirm the presence of the constituents identified by the chromatographic analysis, and the absence of substituents such as pyruvate or succinate.

Figure 3:
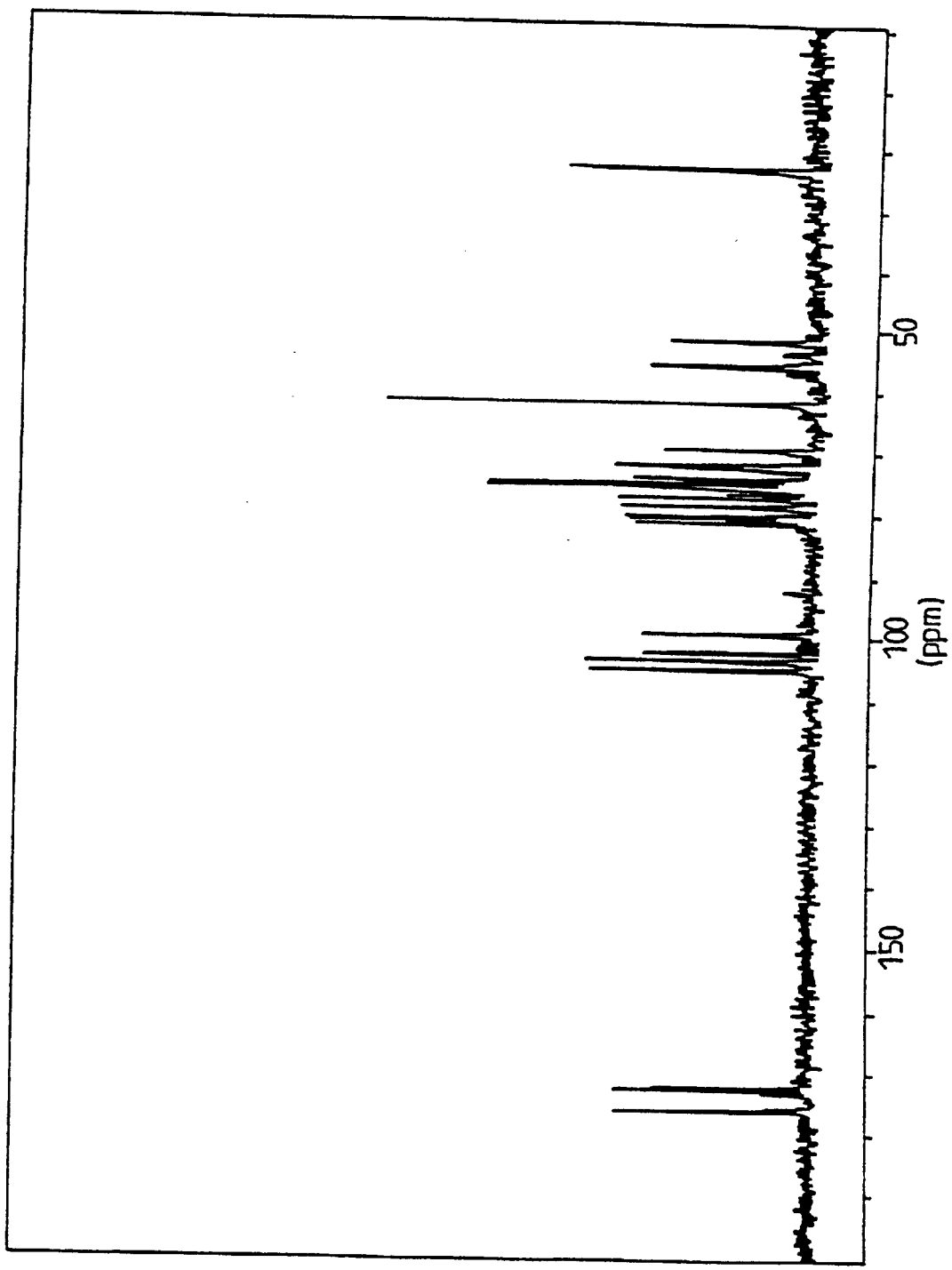
FIG. 3 depicts the $^{13}$C NMR Spectrum of the Exopolysaccharide of *Vibrio diaboticus*.

The $^{13}$C NMR spectrum, represented in FIG. 3, identifies 4 anomeric carbons (100.3, 103.7, 104.9 and 106.3 ppm) as well as 4 carboxyl carbons (173.6, 174.2, 177.0 and 177.3 ppm). Signals at 25.0 ppm and 25.5 ppm can be attributed to methyl or acetyl groups, indicating the N-acetylation of the hexosamines.

c) Rheological studies

The intrinsic viscosity [η] (hydrodynamic volume occupied by one gram of polymer in a given solvent) of the preparation of polysaccharides obtained as described in Example 1, in solution in distilled water supplemented with NaCl at a concentration of 0.1 M, was determined, by establishing flow curves in a dilute mode at various concentrations.

The study of the flow properties of this polymer was also carried out in a semidilute mode on a solution containing 0.3% of polysaccharide. It results in a flow curve giving the relative viscosity ηr as a function of the shear rate, the solution having been subjected continuously to a cycle of increase and decrease in speed.

All the measurements were carried out at 20° C. using a LOW SHEAR 40 viscometer with co-axial cylinders (CONTRAVES).

The intrinsic viscosity was thus evaluated at 570 ml/g.

Figure 4:
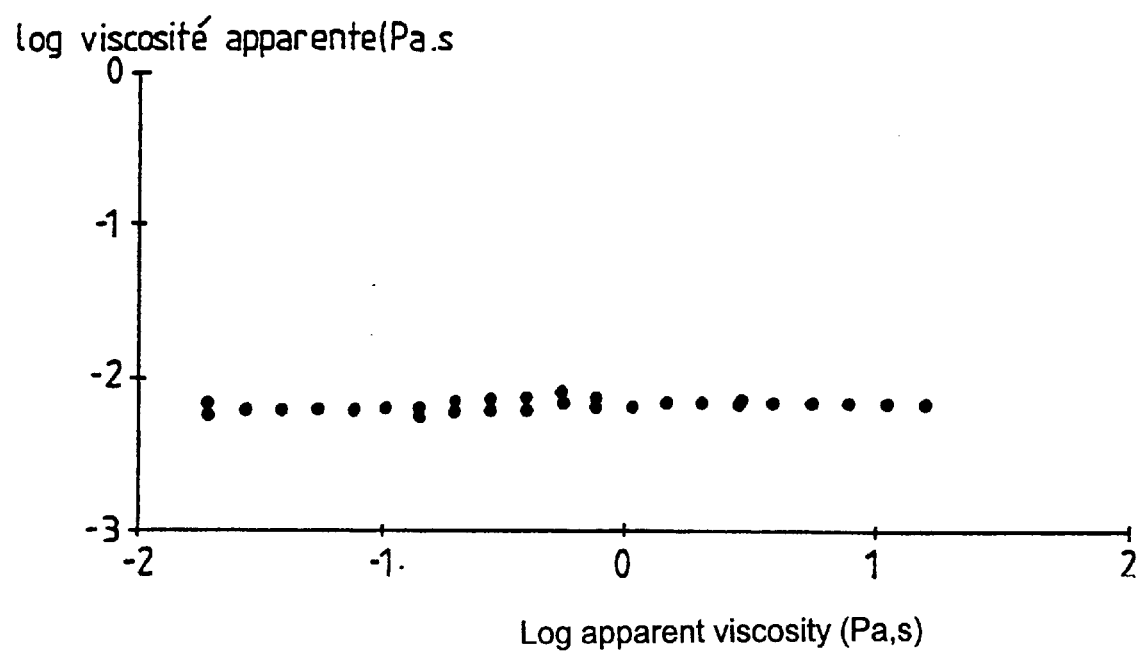
FIG. 4 depicts the Flow Curves for Polysaccharide in 0.1 M NaCl.

The flow curves for this polysaccharide in solution at 0.3% in 0.1 M NaCl are represented in FIG. 4.

What is claimed is:

1. An isolated bacterial strain of the genus Vibrio that belongs to the species called *Vibrio diabolicus*, and possesses the characteristics defined below:

straight Gram-negative bacillus, about 0.8 μm wide and 2.2 μm long;

motile with the aid of a polar flagellum in liquid medium and of peritrichous flagella in solid medium;

non-encapsulated, non-pigmented and non-luminescent;

catalase+, cytochrome oxidase+, chitinase+, faculative anaerobe reducing nitrates to nitrites, and sensitive to 2, 4-diamino-6, 7-diisopropylpteridine;

capable of using, as sole carbon source, any one of the following substrates: glycerol, ribose, galactose, glucose, fructose, mannose, mannitol, N-acetylglucosamine, maltose, sucrose, trehalose, starch, glycogen, gluconate, caprate, citrate and malate;

DNA having a G+C content of 49.6%, a percentage homology of 27% with the DNA of *Vibrio mytili*, a percentage homology of 15% with the DNA of *Vibrio nereis*, and a percentage homology of 5% with the DNA of *Vibrio tubiashii*.

2. The isolated bacterial strain according to claim 1, which possesses the characteristics of the HE800 strain deposited on Oct. 17, 1995 at the CNCM under number I-1629.

3. An isolated bacterial strain, wherein its DNA possesses at least 28% homology with that of the HE800 strain.

4. A process for producing a polysaccharide, said process comprising:
   culturing a bacterial strain according to claim 1; and
   precipitating the polysaccharide from the culture supernatant with ethanol.

5. A process according to claim 4 for producing an exopolysaccharide, wherein:
   the exopolysaccharide does not comprise neutral monosaccharides;
   its content of osamines is about 30±5% by weight;
   its content of uronic acids is about 32±5% by weight;
   its monosaccharide composition, determined after acid methanolysis, is the following: about 11.2% by weight of glucuronic acid, about 18% by weight of N-acetylglucosamine, about 7.9% by weight of N-acetylgalactosamine, that is to say 1.4 m61 of N-acetylglucosamine and 0.6 mol of N-acetylgalactosamine per 1 mol of glucuronic acid;
   it does not comprise sulphated saccharide units;
   its intrinsic viscosity is of the order of 570 ml/g;
   its mean molecular weight is of the order of 800,000 Da.

6. A process according to claim 4 wherein said bacterial strain is the HE800 strain deposited on Oct. 17, 1995 at the CNCM under No. I-1629.

7. A process for producing a medicament, said process comprising
   culturing a bacterial strain according to claim 1;
   precipitating the polysaccharide from the culture supernatant with ethanol; and
   producing a medicament by incorporating the polysaccharide therein as an active agent.

* * * * *